United States Patent

Hendricks

[11] 4,213,813
[45] Jul. 22, 1980

[54] SANITARY NAPKIN

[76] Inventor: Laurel A. Hendricks, P.O. Box 943, Palo Alto, Calif. 94302

[21] Appl. No.: 953,782

[22] Filed: Oct. 23, 1978

[51] Int. Cl.² .................. B32B 31/16; B32B 3/04; A61F 13/16

[52] U.S. Cl. .................. 156/226; 128/284; 128/287; 128/290 R; 156/216; 156/227; 156/290

[58] Field of Search .......... 128/284, 287, 290 R; 156/227, 290, 216, 226

[56] References Cited

U.S. PATENT DOCUMENTS

| | | | |
|---|---|---|---|
| 3,230,955 | 1/1966 | Joa et al. | 128/290 R |
| 3,454,008 | 7/1969 | Hendricks | 128/290 R |
| 3,865,112 | 2/1975 | Roeder | 128/290 R |
| 3,868,287 | 2/1975 | Lewyckyj | 156/227 X |
| 3,888,254 | 6/1975 | Hendricks | 128/290 R |
| 3,911,921 | 10/1975 | Svensson | 128/290 R |
| 4,029,101 | 6/1977 | Chesky et al. | 128/290 R |

*Primary Examiner*—William A. Powell
*Assistant Examiner*—Robert A. Dawson
*Attorney, Agent, or Firm*—Linval B. Castle

[57] ABSTRACT

An easily manufactured sanitary napkin, adhesively securable to an undergarment, includes a rectangular fabric sheet, two-thirds of which is covered with a sheet of moisture barrier. A highly absorbent filler pad shorter than the cover layer is inserted on the center third of the fabric sheet and between that sheet and the moisture barrier. The uncovered third of the fabric is then folded over the top of the center third and contacts the moisture barrier overlaying the filler pad. The opposite third with the barrier is folded over the midsection layers to form the napkin. The tab ends of the foldover fabric and barrier layers extending beyond the ends of the filler pad are then heat-pressure sealed together and an adhesive strip having a peel-off backing strip is applied to each of the tab ends that are a continuous and integral part of the napkin.

4 Claims, 7 Drawing Figures

U.S. Patent
Jul. 22, 1980
4,213,813
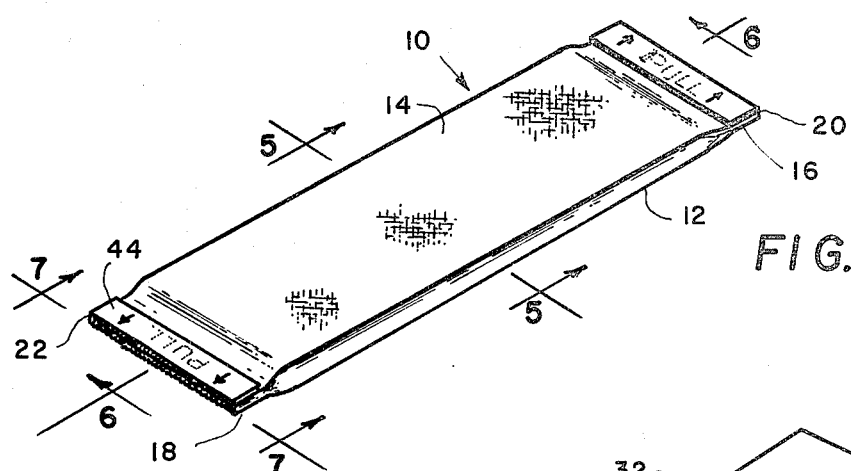
FIG. 1
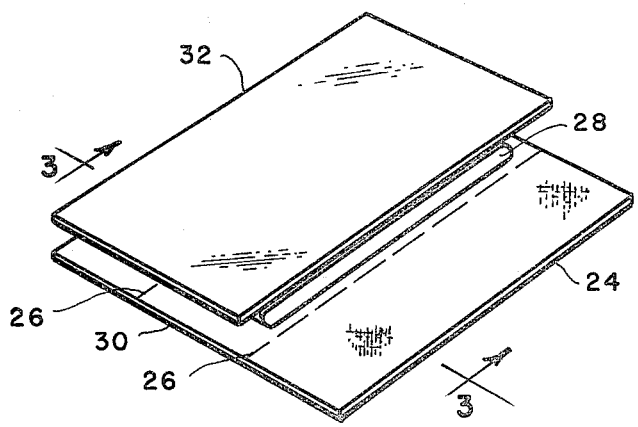
FIG. 2
FIG. 3
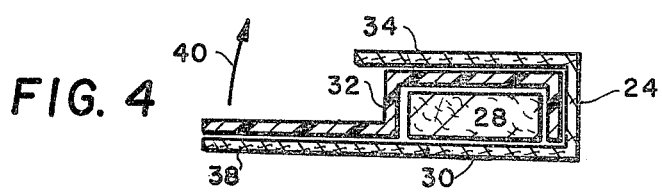
FIG. 4
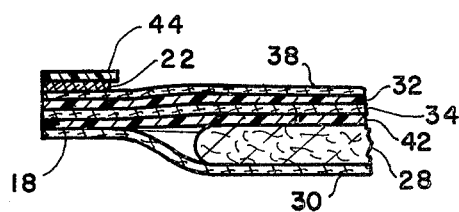
FIG. 7
FIG. 6
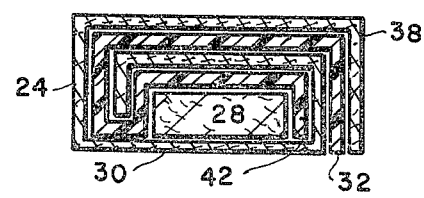
FIG. 5

SANITARY NAPKIN

BACKGROUND OF THE INVENTION

This invention relates to sanitary napkins, and particularly to an improved, easily-manufactured, adhesively secured napkin with integral moisture barriers.

Sanitary napkins incorporating moisture barriers and adhesive strips to releasably secure them to garments are very well known, several being described in my U.S. Pat. No. 3,888,254, issued June 10, 1975. Some of the prior art napkins employ a single longitudinal adhesive strip extending substantially the entire length of the pad and other types employ adhesive attachments at each tab end. The tab end attachment type tends to be superior over the single longitudinal adhesive strip in that it reduces the tendency of the outer layer, or garment side of the pad, to separate from the filler, thereby permitting the moisture barriers to shift or incline from their original position to lower the effectiveness of the moisture barriers.

While some sanitary napkin designs employ lateral adhesive strips at each tab end, they still suffer a serious defect in that the lateral adhesive strips adhere only to the surface layer of the cover fabric. Therefore, the remaining layers are free to curl or double over during use. These prior art defects are overcome by the present invention.

Briefly described, the sanitary napkin of the present invention comprises an absorbent filler pad wrapped with absorbent fabric layers and moisture barriers, and having lateral adhesive strips on each tab. The pervious material and the moisture barrier layers are integrally formed by the simple process of heat-pressure bonding, while the layers that extend beyond the ends of the filler pad are more rigidly bonded while simultaneously crimped to form tab ends that do not separate or curl over during use. The napkin pad itself is formed of a rectangular non-woven fabric sheet, two-thirds of which is covered with a sheet of moisture barrier. The highly absorbent filler pad is shorter than the fabric sheet and is inserted on the center third of the fabric sheet and between that sheet and the moisture barrier. The fabric third that is uncovered by the moisture barrier is folded over the top of the center third and is in direct contact with the moisture barrier. The opposite third having the moisture barrier is folded over the top of the center third. These alternating layers extend beyond the ends of the filler pad. Heat and pressure is applied to bond the layers together, with higher pressure being applied to the tab ends to securely bond and crimp together the tab ends. An adhesive strip with a peel-off protecting strip may then be applied to the tab ends.

The advantages of the sanitary napkin of the invention are that the fused and crimped adhesive tab ends prevent separation of the layers so that the napkin remains completely intact without curling or doubling over during use. In addition, the pad adjusts very readily to body activity and permits a lengthwise "pull" or stress on the entire pad rather than just on the fabric layer that is attached to the undergarment. Furthermore, the napkin is not bulky or bunchy since its positioning during use is determined by the end-to-end attachment which allows for a certain amount of undergarment "give" without interference with its comfortable and indiscernible attachment.

Another important advantage is that the napkin comprises a comparatively simple manufacturing design that may be easily produced in various desired sizes.

DESCRIPTION OF THE DRAWINGS

In the drawings which illustrate the preferred embodiment of the invention:

FIG. 1 is a perspective view illustrating the sanitary napkin constructed in accordance with the principles of the invention;

FIG. 2 is an exploded perspective view illustrating components of the napkin of the present invention prior to their assembly;

FIGS. 3, 4 and 5 are cross-sectional elevation views of the steps in assembling the napkin of the invention, with FIG. 3 representing a view taken along the lines 3—3 of FIG. 2;

FIG. 6 is a cross-sectional view of a portion of the napkin taken along the lines 6—6 of FIG. 1; and FIG. 7 is an end view taken along the lines 7—7 of FIG. 1.

DETAILED DESCRIPTION OF THE PREFERRED EMBODIMENT

As illustrated in the perspective drawing of FIG. 1, the sanitary napkin, generally illustrated by the reference numeral 10, comprises an elongated fabric-covered pad having an absorbent surface 12 and a moisture-proof surface 14. At each of the narrow ends of the pad, fabric layers overlying the core or absorbent filler are pressed together and heat-pressure sealed and crimped, as shown, to form unitary but flexible tab ends 16 and 18. Overlying each of these tab ends 16 and 18 and on the moisture-proof surface 14 are adhesive strips 20 and 22, each suitably covered with a peel-off strip which preferably has an extended liner which is readily removed to expose the adhesive surface. Since the end tabs 16 and 18 are heat and pressure bonded together or fused and crimped, the adhesive strips are effectively connected to all layers forming the end tabs, so that the adhesive strips and all fabric and moisture barrier layers forming the end tab become the unitary strip which very effectively prevents the various component layers from shifting with respect to each other during use.

FIGS. 2 through 5 illustrate the steps in the construction of the sanitary napkin. In the perspective drawing of FIG. 2, a rectangular sheet of a thin soft absorbent non-woven fabric is, in effect, divided into three substantially equal sections as shown by the dashed lines 26, each section being substantially the desired length and width of the completed napkin pad. A highly absorbent filler pad 28, such as soft absorbent cotton which may, if desired, be covered with a layer of soft absorbent crepe paper, is placed on the center third 30 of the non-woven fabric sheet 24. The filler pad 28 should be somewhat shorter than the length of the section 30. Overlying at least two-thirds of the fabric sheet 24 and substantially flush with three edges of that sheet is a moisture barrier sheet 32 formed of a suitable vinyl or chemical material.

As best illustrated in FIG. 3, the one-third section 34 of the non-woven fabric sheet 24 not covered by the moisture barrier 32 is then folded up over the filler pad 28 and moisture barrier 32 as illustrated by the arrow 36, as shown in the cross-sectional view of FIG. 4. Then, as illustrated in FIG. 4, the third section 38 of the fabric sheet 24 that is covered by the moisture barrier 32 is folded in a direction indicated by the arrow 40 so that the section 38 of the fabric sheet 24, together with its overlying moisture barrier, is folded on top of the section 34 of the fabric sheet 24, as best illustrated in FIG. 5. The napkin therefore comprises an absorbent filler pad 28 covered with a single layer of non-woven fabric 30 on the absorbent surface and on the moisture-proof surface with two layers of fabric sections 34 and 38 separated by two layers 32 and 42 of moisture barrier. The moisture barrier layers 32 and 42 are preferably wrapped down around the side edges of the filler pad 28 so that the filler pad may be exposed to moisture only through the surface section 30 of the fabric sheet 24, and the fabric sections 34 and 38 are heat-pressure bonded together with the barrier layers 32 and 42 to form a unitary non-separable pad.

As previously mentioned, the non-woven fabric sheet 24 and the moisture barrier sheet 32 extend beyond the ends of the filler pad 28 to provide end tabs. As illustrated in FIG. 6, all layers of the fabric sheet 30, 34 and 38 and of the moisture barriers 32 and 42 are pressed together in a hot crimping press so that the alternate sheets of moisture barrier 32 and 42 are fused together with their adjacent fabric sheets 30, 34 and 38 to form a solid unitary but resilient end tab 18, as best illustrated in FIG. 7. After the end tabs have been formed by the heat-press crimping operation, an adhesive strip 22 is applied so that the adhesive becomes part of the unitary tab 18. For ease in handling, the adhesive 22 is provided with a non-adhesive peel-off strip or tab 44 that preferably carries the instruction that the tab 44 should be peeled from the center of the pad outward as illustrated in FIG. 1.

Having thus described my invention, what is claimed is:

1. A method of making a sanitary napkin comprising the steps of:
    providing a rectangular sheet of thin absorbent fabric having a width equal to substantially thrice the desired width of the napkin and a length substantially the total desired length of said napkin including end tabs;
    centering an absorbent pad in the central third of said fabric sheet, said pad having a width substantially equal to the desired width of said napkin and a length equal to the desired length of said napkin excluding end tabs;
    providing a sheet of moisture barrier material over said pad and over one of said exposed thirds of said fabric sheet;
    folding the uncovered third of said fabric sheet over the top of said pad and its covering moisture barrier;
    folding the third of said fabric sheet and its covering moisture barrier over said uncovered third; and
    sealing together all fabric and moisture barrier layers and sealing those layers extending beyond the ends of said pad into a unitary end tab at each end of said pad.

2. The method claimed in claim 1 wherein said step of sealing said unitary end tab includes the process of heating, pressing, and crimping.

3. The method claimed in claim 2 including the further step of:
    attaching a lateral strip of adhesive material to each tab, said material being attached on the tab surface corresponding to the napkin moisture barrier surface and with its adhesive surface exposed.

4. The method claimed in claim 3 wherein said exposed adhesive surface is covered with a non-adhesive peel-off strip.

* * * * *